(12) United States Patent
Boymond et al.

(10) Patent No.: US 6,432,326 B1
(45) Date of Patent: Aug. 13, 2002

(54) METHOD FOR THE STEREOSELECTIVE PRODUCTION OF GRIGNARD COMPOUNDS AND USE THEREOF

(75) Inventors: Laure Boymond, Versailles (FR); Mario Rottländer, Marburg (DE); Gerard Cahiez, Paris (FR); Paul Knochel, Marburg (DE)

(73) Assignee: BASF Aktiengesellschaft, Ludwigshafen (DE)

( * ) Notice: Subject to any disclaimer, the term of this patent is extended or adjusted under 35 U.S.C. 154(b) by 0 days.

(21) Appl. No.: 09/720,883

(22) PCT Filed: Jul. 2, 1999

(86) PCT No.: PCT/EP99/04593

§ 371 (c)(1),
(2), (4) Date: Jan. 2, 2001

(87) PCT Pub. No.: WO00/02928

PCT Pub. Date: Jan. 20, 2000

(30) Foreign Application Priority Data

Jul. 9, 1998 (DE) .......................................... 198 30 599

(51) Int. Cl.$^7$ ................................................. C07F 3/02
(52) U.S. Cl. ............................... 260/665 G; 260/665 R
(58) Field of Search ........................... 260/665 G, 665 R

(56) References Cited

U.S. PATENT DOCUMENTS

| | | | |
|---|---|---|---|
| 3,428,616 A | | 2/1969 | Greer |
| 3,856,867 A | | 12/1974 | Ramsden |
| 4,293,497 A | | 10/1981 | Cardenas |
| 5,286,726 A | * | 2/1994 | Bey et al. .................... 514/249 |
| 5,519,021 A | * | 5/1996 | Young et al. ............. 514/230.5 |
| 6,184,419 B1 | * | 2/2001 | Berg-Schultz et al. ...... 568/374 |

FOREIGN PATENT DOCUMENTS

| | | |
|---|---|---|
| CA | 2260023 | 1/1998 |
| DE | 196 28159 | 1/1998 |
| EP | 414 106 | 2/1991 |
| GB | 948714 | 2/1964 |

OTHER PUBLICATIONS

CA:101:72782 abs of Angew. Chem. by Benn et al 96(7), pp 521–523, 1984.*
Journal of Organometallic Chemistry vol. 2 by Martin et al pp. 380–387, 1964.*
CA:88:89834 abs of CA169418 Jul. 1976.*
CA:108:112708 abs of Am. Chem. Soc. by Hackett et al 110(5) pp 1449–1462 1988.*
Angew.Chem., vol. 108,1996:2436.
J. FluorineChem.1982, 20,699.
J.Organomet.Chem., 1976,113:107.
Am.Chem.Soc., vol. 94, 1972:4374, Tamao et al.
Acc.Chem.Res.1991,24,257–263, Luh et al.
J.Org.Chem.1976,1972:4374.
J.Poly.Sci,PartA–1,vol. 7, 3245–3255(1969)Minoura et al.
Org.React., vol. 22, 1975;253, Posner.

* cited by examiner

Primary Examiner—Jean F. Vollano
(74) Attorney, Agent, or Firm—Keil & Weinkauf

(57) ABSTRACT

A process for the stereoselective preparation of Grignard compounds of the formula I and polymer-bonded compounds of the formula Ia is described. The process can be used for producing substance reference libraries and the compounds of the formulae I and Ia can be used in stereoselective chemical synthesis.

7 Claims, No Drawings

METHOD FOR THE STEREOSELECTIVE PRODUCTION OF GRIGNARD COMPOUNDS AND USE THEREOF

This application is a 371 of PCT/EP99/04593 filed Jul. 2, 1999, now WO 00/029,281.

The present invention relates to a process for the stereoselective preparation of Grignard compounds of the formula I. The invention also relates to polymer-immobilized compounds of the formula Ia. The invention further relates to the use of the process for producing substance reference libraries and to the use of the compounds of the formulae I and Ia in stereoselective chemical synthesis.

Grignard compounds are valuable intermediates in organic synthesis. They are one of the most important classes of compounds in organic synthetic chemistry. Their reaction with electrophilic substances allows the preparation of a wide variety of compounds. Many syntheses in which Grignard compounds are used are known from the literature (see: Handbook of Grignard Reagents, Eds. G. S. Silverman, P. E. Rakita, Marcel Dekker, Inc., 1996). Grignard compounds have a good reactivity at a satisfactory chemoselectivity (cf. Posner G. H. Org. React., Vol. 22, 1975: 253, Lipshutz et al., Org. React., Vol. 41, 1992: 135, Luh T. -Y. Chem. Res., Vol. 24, 1991: 257 or Tamao et al., J. Am. Chem. Soc., Vol. 94, 1972: 4374).

Alkenyl Grignard compounds are usually prepared by reacting a corresponding alkenyl halide with metallic magnesium or another source of magnesium. A further method starts from acetylenes which are carbometallated with Grignard compounds in the presence of suitable promoters. The methods for this are known to those skilled in the art and may be found, for example, in Houben-Weyl, Vol. XIII/2a and the literature cited therein and in Handbook of Grignard Reagents, Eds. G. S. Silverman, P. E. Rakita, Marcel Dekker, Inc., 1996 or in J. Organomet. Chem. 1976, 113: 107 or in J. Fluorine Chem. 1982, 20, 699.

The preparation of vinylic Grignard compounds by these methods is, however, often accompanied by secondary reactions (e.g. eliminations) and is not applicable to all vinyl halides. Thus, for example, terminal, vinylic halides usually react very unsatisfactorily to give the desired Grignard compound. Under the reaction conditions employed, an isomerization as shown in Scheme I is often observed.

Scheme I: Isomerization of Grignard Compounds

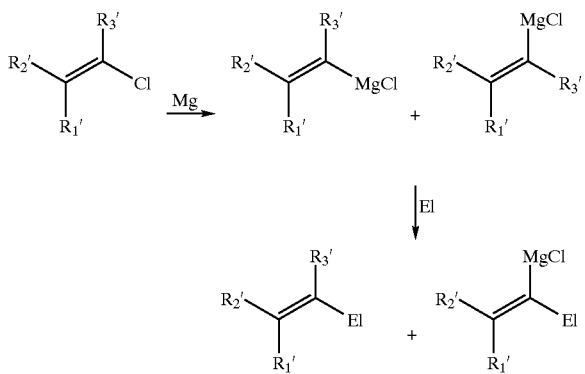

A cis halide (based on halogen and $R_1'$) gives a mixture of the trans/cis isomeric Grignard compounds which then in the further reaction with the electrophil (=E1) give a trans/cis mixture of the desired products. The radicals $R_1'$, $R_2'$ and $R_3'$ are shown only schematically in Scheme I.

A further disadvantage of the methods available hitherto is that they do not allow the preparation of Grignard compounds having further functional groups, for example esters, nitriles or amides, which would react with an electrophil, since such groups would react in the preparation of the Grignard compound.

It is an object of the present invention to make available a process for the synthesis of vinylic Grignard compounds which provides a stereoselective route to these compounds with retention of the original trans/cis geometry. A further object is to make possible the further stereoselective reaction of these compounds with electrophils. Another object is to provide a process which tolerates many additional functional groups in the molecule in order to be able to prepare synthetically and pharmacologically interesting compounds. We have found that this object is achieved by a process for preparing compounds of the formula I

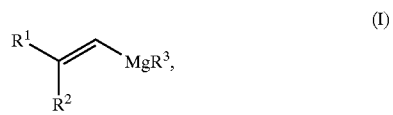
(I)

which comprises stereoselectively reacting compounds of the formula II

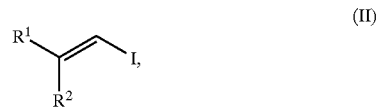
(II)

with compounds of the formula $R^3MgX$ (III) at below +30° C. to give compounds of the formula I,
where the substituents and variables in the formulae I, II and III have the following meanings:
X=halogen such as Cl or $R^3$,
$R^1$=substituted or unsubstituted, branched or unbranched $C_1$–$C_{10}$-alkyl, $C_3$–$C_{10}$-cycloalkyl, $C_1$–$C_4$-alkylaryl, $C_1$–$C_4$-alkylheteroaryl, aryl or heteroaryl,
$R^2$=hydrogen, —$CH_2$—$R^4$,
$R^3$=branched or unbranched $C_1$–$C_{10}$-alkyl, $C_3$–$C_{10}$-cycloalkyl,
$R^4$=hydrogen, substituted or unsubstituted, branched or unbranched —$OC_1$–$C_{10}$-alkyl, —$OC_3$–$C_{10}$-cycloalkyl, —$OC_1$–$C_4$-alkylaryl, —$OC_1$–$C_4$-alkylheteroaryl, —$OCNR^1R^5$, $R^6$,
$R^5$=as $R^1$, but independently thereof,
$R^6$=a solid support.

In the compounds of the formulae I and II, $R^1$ is substituted or unsubstituted, branched or unbranched $C_1$–$C_{10}$-alkyl, $C_3$–$C_{10}$-cycloalkyl, $C_1$–$C_4$-alkylaryl, $C_1$–$C_4$-alkylheteroaryl, aryl, heteroaryl or $R^5$.

Examples of alkyl radicals are substituted or unsubstituted, branched or unbranched $C_1$–$C_{10}$-alkyl chains such as methyl, ethyl, n-propyl, 1-methylethyl, n-butyl, 1-methylpropyl, 2-methylpropyl, 1,1-dimethylethyl, n-pentyl, 1-methylbutyl, 2-methylbutyl, 3-methylbutyl, 2,2-dimethylpropyl, 1-ethylpropyl, n-hexyl, 1,1-dimethylpropyl, 1,2-dimethylpropyl, 1-methylpentyl, 2-methylpentyl, 3-methylpentyl, 4-methylpentyl, 1,1-dimethylbutyl, 1,2-dimethylbutyl, 1,3-dimethylbutyl, 2,2-dimethylbutyl, 2,3-dimethylbutyl, 3,3-dimethylbutyl, 1-ethylbutyl, 2-ethylbutyl, 1,1,2-trimethylpropyl, 1,2,2-trimethylpropyl, 1-ethyl-1-methylpropyl, 1-ethyl-2-methylpropyl, n-heptyl, n-octyl, n-nonyl or n-decyl.

Examples of cycloalkyl radicals in the formula are substituted or unsubstituted, branched or unbranched $C_3$-$C_{10}$- cycloalkyl chains having from 3 to 7 carbon atoms in the ring or ring system, e.g. cyclopropyl, cyclobutyl, cyclopentyl, cyclohexyl, cycloheptyl, 1-methylcyclopropyl, 1-ethylcyclopropyl, 1-propylcyclopropyl, 1-butylcyclopropyl, 1-pentylcyclopropyl, 1-methyl-1-butylcyclopropyl, 1,2-dimethylcyclopropyl, 1-methyl-2-ethylcyclopropyl, cyclooctyl, cyclononyl or cyclodecyl. The cycloalkyl radicals can also have heteroatoms such as S, N and O in the ring. The cycloalkyl radicals can have branched or unbranched alkyl groups.

Examples of $C_1$–$C_4$-alkylaryl are substituted or unsubstituted, branched or unbranched $C_1$–$C_4$-alkylphenyl or $C_1$–$C_4$-alkylnaphthyl radicals such as methylphenyl, ethylphenyl, propylphenyl, 1-methylethylphenyl, butylphenyl, 1-methylpropylphenyl, 2-methylpropylphenyl, 1,1-dimethylethylphenyl, methylnaphthyl, ethylnaphthyl, propylnaphthyl, 1-methylethylnaphthyl, butylnaphthyl, 1-methylpropylnaphthyl, 2-methylpropylnaphthyl or 1,1-dimethylethylnaphthyl.

Examples of alkylheteroaryl radicals are substituted or unsubstituted, branched or unbranched $C_1$–$C_4$-alkylheteroaryl radicals which have one or more nitrogen, sulfur and/or oxygen atoms in the ring or ring system.

Examples of aryl radicals are substituted or unsubstituted aryls such as phenyl, naphthyl or aromatic rings or ring systems having from 6 to 18 carbon atoms in the ring system and also up to 24 further carbon atoms which can form further nonaromatic rings or ring systems having from 3 to 8 carbon atoms in the ring. Preference is given to substituted or unsubstituted phenyl or naphthyl.

Examples of heteroaryl radicals are simple or condensed aromatic ring systems having one or more heteroaromatic 3- to 7-membered rings which may contain one or more heteroatoms such as N, O or S.

Possible substituents on the radicals $R^1$ are in principle all conceivable substituents except for ketones or aldehydes, for example one or more substituents such as halogen, e.g. fluorine, chlorine or bromine, cyano, nitro, amino, hydroxy, alkyl, cycloalkyl, aryl, alkoxy, benzyloxy, phenyl or benzyl.

$R^2$ in the formulae I and II is hydrogen or —$CH_2$—$R^4$.

In the formula $R^3MgX$ (III), $R^3$ is branched or unbranched $C_1$–$C_{10}$-alkyl or $C_3$–$C_{10}$-cycloalkyl.

Examples of alkyl radicals are substituted or unsubstituted, branched or unbranched $C_1$–$C_{10}$-alkyl chains such as methyl, ethyl, n-propyl, 1-methylethyl, n-butyl, 1-methylpropyl, 2-methylpropyl, 1,1-dimethylethyl, n-pentyl, 1-methylbutyl, 2-methylbutyl, 3-methylbutyl, 2,2-dimethylpropyl, 1-ethylpropyl, n-hexyl, 1,1-dimethylpropyl, 1,2-dimethylpropyl, 1-methylpentyl, 2-methylpentyl, 3-methylpentyl, 4-methylpentyl, 1,1-dimethylbutyl, 1,2-dimethylbutyl, 1,3-dimethylbutyl, 2,2-dimethylbutyl, 2,3-dimethylbutyl, 3,3-dimethylbutyl, 1-ethylbutyl, 2-ethylbutyl, 1,1,2-trimethylpropyl, 1,2,2-trimethylpropyl, 1-ethyl-1-methylpropyl, 1-ethyl-2-methylpropyl, n-heptyl, n-octyl, n-nonyl or n-decyl.

Examples of cycloalkyl radicals in the formula III are substituted or unsubstituted, branched or unbranched $C_3$-$C_{10}$-cycloalkyl chains having from 3 to 7 carbon atoms in the ring or ring system, e.g. cyclopropyl, cyclobutyl, cyclopentyl, cyclohexyl, cycloheptyl, 1-methylcyclopropyl, 1-ethylcyclopropyl, 1-propylcyclopropyl, 1-butylcyclopropyl, 1-pentylcyclopropyl, 1-methyl-1-butylcyclopropyl, 1,2-dimethylcyclopropyl, 1-methyl-2-ethylcyclopropyl, cyclooctyl, cyclononyl or cyclodecyl.

In principle, the radicals mentioned under $R^3$ can also bear substituents, but since these compounds are complicated to prepare and the radical $R^3$ is not present in the products synthesized from the Grignard compounds, it is more sensible from an economic point of view to use the unsubstituted compounds which are commercially available or can be synthesized simply.

$R^4$ is hydrogen, substituted or unsubstituted, branched or unbranched —$OC_1$–$C_{10}$-alkyl, —$OC_3$–$C_{10}$-cycloalkyl, —$OC_1$–$C_4$-alkylaryl, —$OC_1$–$C_4$-alkylheteroaryl, $OCNR^1R^5$ or $R^6$=4-hydroxybenzylpolystyrene.

Examples of —O-alkyl radicals are substituted or unsubstituted, branched or unbranched —$OC_1$–$C_{10}$-alkyl chains. In these —O-alkyl radicals, the $C_1$–$C_{10}$-alkyl chains are, for example: methyl, ethyl, n-propyl, 1-methylethyl, n-butyl, 1-methylpropyl, 2-methylpropyl, 1,1-dimethylethyl, n-pentyl, 1-methylbutyl, 2-methylbutyl, 3-methylbutyl, 2,2-dimethylpropyl, 1-ethylpropyl, n-hexyl, 1,1-dimethylpropyl, 1,2-dimethylpropyl, 1-methylpentyl, 2-methylpentyl, 3-methylpentyl, 4-methylpentyl, 1,1-dimethylbutyl, 1,2-dimethylbutyl, 1,3-dimethylbutyl, 2,2-dimethylbutyl, 2,3-dimethylbutyl, 3,3-dimethylbutyl, 1-ethylbutyl, 2-ethylbutyl, 1,1,2-trimethylpropyl, 1,2,2-trimethylpropyl, 1-ethyl-1-methylpropyl, 1-ethyl-2-methylpropyl, n-heptyl, n-octyl, n-nonyl or n-decyl.

Examples of —O-cycloalkyl radicals in the radicals $R^4$ are substituted or unsubstituted, branched or unbranched —$OC_3$—$C_{10}$—cycloalkyl chains having from 3 to 7 carbon atoms in the ring or ring system, where the $C_3$—$C_{10}$—cycloalkyl chains in these —$OC_3$—$C_{10}$—cycloalkyl chains are, for example: cyclopropyl, cyclobutyl, cyclopentyl, cyclohexyl, cycloheptyl, 1-methylcyclopropyl, 1-ethylcyclopropyl, 1-propylcyclopropyl, 1-butylcyclopropyl, 1-pentylcyclopropyl, 1-methyl-1-butylcyclopropyl, 1,2-dimethylcyclypropyl, 1-methyl-2-ethylcyclopropyl, cyclooctyl, cyclononyl or cyclodecyl. The cycloalkyl radicals can also have heteroatoms such as S, N and O in the ring. The cycloalkyl radicals can have branched or unbranched alkyl groups.

Examples of —O—$C_1$–$C_4$-alkylaryl are substituted or unsubstituted, branched or unbranched —O—$C_1$–$C_4$-alkylaryl radicals, where the $C_1$–$C_4$-alkylaryl chains are, for example: $C_1$—$C_4$—alkylphenyl or $C_1$—$C_4$—alkylnaphthyl radicals such as methylphenyl, ethylphenyl, propylphenyl, 1-methylethylphenyl, butylphenyl, 1-methylpropylphenyl, 2-methylpropylphenyl, 1,1-dimethylethylphenyl, methylnaphthyl, ethylnaphthyl, propylnaphthyl, 1-methylethylnaphthyl, butylnaphthyl, 1-methylpropylnaphthyl, 2-methylpropylnaphthyl or 1,1-dimethylethylnaphthyl.

Examples of —O-alkylheteroaryl radicals are substituted or unsubstituted, branched or unbranched —O—$C_1$—$C_4$—alkylheteroaryl radicals which have one or more nitrogen, sulfur and/or oxygen atoms in the ring or ring system. The heteroaromatic part can comprise simple or condensed aromatic rings or ring systems together with one or more heteroaromatic 3- to 7-membered rings.

All the radicals mentioned above have substituent $R^4$ bound via the oxygen.

$R^4$ can also be a polymer (=solid support) $R^6$ (for definition of the support, see below). The polymer used is advantageously 4-hydroxybenzylpolystyrene.

$OCNR^1R^5$ are carbamates [sic] in which $R^1$ and $R^5$ are, independently of one another, as defined above.

Possible substituents on the specified radicals $R^4$ are, in principle, all conceivable substituents apart from ketones or aldehydes, for example one or more substituents such as halogen, e.g. fluorine, chlorine or bromine, cyano, nitro, amino, hydroxy, alkyl, cycloalkyl, aryl, alkoxy, benzyloxy, phenyl or benzyl.

The reaction of the process of the present invention is advantageously carried out by reacting the compounds of the formula II, advantageously in an inert, aprotic solvent, for example ethers such as tetrahydrofuran (=THF), diethyl ether, dioxane, dimethoxyethane or methyl tert-butyl ether (=MTB), at below 30° C., preferably from −100° C. to +30° C., particularly preferably from −90° C. to +30° C., very particularly preferably from −80° C. to +25° C., with a compound of the formula $R^3MgX$ (III) to give a compound of the formula I. In the case of compounds in which the radical $R^4$ is bound via an oxygen atom, it is advantageous to select a reaction temperature of less than −20° C., preferably from −100° C. to −20° C., particularly preferably from −80° C. to −40° C. In the case of compounds in which the radical $R^4$ is bound via a carbon atom, it is advantageous to select a reaction temperature of less than +30° C., preferably from −40° C. to +30° C., particularly preferably from −20° C. to +30° C., very particularly preferably from 0° C. to +30° C. In principle, all compounds of the formula $R^3MgX$ known to those skilled in the art can be used for preparing the Grignard compound; preference is given to using diisopropylmagnesium or isopropylmagnesium chloride.

Under these mild conditions, the halogen-magnesium exchange occurs without the Grignard compounds of the formula I (see above) which are formed reacting with the further functional groups present in the molecule. The compounds react only in the desired manner, stereoselectively with the electrophil (see Examples in Table I). trans/cis ratios of greater than 85:15, preferably of 90:10, particularly preferably of 98:2, are achieved.

The reaction time is from 1 hour to 18 hours, depending on the vinyl halide used.

A particular advantage of this process is that polymer-bonded alcohols (=$R^4$=$R^6$=polymer, solid support) also undergo the halogen-magnesium exchange in the desired manner. Like the free alcohols, these alcohols serve as starting compounds for the synthesis of compounds of the formula II. The use of polymer-bonded alcohols allows the following compounds of the formula Ia to be prepared:

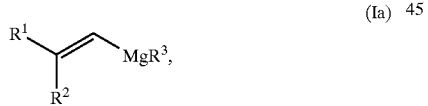

(Ia)

where the radical $R^2$ is —$CH_2$—$R^4$, $R^4$ is $R^6$ and $R^6$ is a solid support.

The compounds of the formula Ia can advantageously be bound to a solid support (=$R^6$) as is known from solid-phase peptide synthesis. Possible supports can consist of a wide variety of materials as long as they are compatible with the synthetic chemistry employed. In these, the size, size distribution and shape of the supports can be varied within a wide range, depending on the material. Preference is given to spherical particles which advantageously have a homogeneous size distribution.

Examples of preferred solid supports are functionalized crosslinked polystyrenes such as 4-hydroxybenzylpolystyrene.

The compound can be bound to the support or polymeric support by means of reactions known to those skilled in the art, as may be found, for example, in the review by Balkenhohl et al. (Angew. Chem., Vol. 108, 1996: 2436) and the literature cited therein. In the case of Wang resin, the compound can be bound, for example, via an ester. After the synthesis is complete, this can be cleaved from the resin using, for example, trifluoroacetic acid.

This procedure makes it possible to utilize the advantages of solid-phase synthesis, namely the ability to carry out the reaction automatically and work up the reaction mixture by simple washing and filtration. Use of the process of the present invention thus allows substance reference libraries to be produced easily.

This reaction is thus very suitable for producing substance reference libraries by the principles of combinatorial chemistry or of NSA (Angew. Chem., Vol. 108, 1996: 2436), in which the halogen-magnesium exchange is first carried out on a starting material bound to a polymer and the product is then reacted with many electrophils (in a vessel for producing mixtures).

After washing and filtering, the target products are then detached from the polymer under conditions suitable for cleavage of the linking bond.

The novel compounds of the formula I or Ia (=$R^4$=$R^6$= solid support, preferably polymeric support) can advantageously be used in chemical synthesis as starting materials or intermediates which can be employed in a wide variety of subsequent reactions. Examples are synthesis of carotinoids, vitamins or active compounds, for example active compounds for pharmaceuticals or crop protection products.

The following examples illustrate the invention without constituting a limitation of the method:

EXAMPLES

A. Preparation of trans-4-(4-Carbethoxybenzyloxy)-2-phenyl-1-iodopropene

A solution of 700 mg (1.66 mmol) of trans-4-(4-carbethoxy-benzyloxy)-2-phenyl-1-iodopropene in 4 ml of THF was cooled to −85° C. and 3.9 ml (3.32 mmol) of a solution of diisopropylmagnesium in THF (0.85 M) were added. After 16 hours at −70° C., 0.48 ml (4.65 mmol) of benzaldehyde was added. After 3 hours, the reaction mixture was hydrolyzed and the organic phase was evaporated. Chromatography of the crude product using $CH_2Cl_2$/ether 95:5 4/1 gave 528 mg (79%) of the alcohol.

Table I shows the results of analogous reactions with various electrophils.

The starting compounds (Grignard compounds) were prepared by an iodine-magnesium exchange over 7–28 hours. The temperature of the reaction solutions was within the range from −78 to +25° C. Good conversions could be achieved at these temperatures.

The yields given in Table I are based on chemically pure end product.

TABLE I

Preparation of Grignard compounds and reaction with electrophils

| Vinyl halide | Electrophil | Product | Yield (%) |
|---|---|---|---|
| C₆H₁₂–CH=CH–I | TsCN | C₆H₁₂–CH=CH–CN | 71 |
| C₆H₁₂–CH=CH–I | PhCHO | C₆H₁₂–CH=CH–CH(OH)Ph | 60 |
| Ph(MeOCH₂)C=CH–I | PhCHO | Ph(MeOCH₂)C=CH–CH(OH)Ph | 95 |
| Ph-C(=CH–I)–CH₂–O–CH₂–(3-NC-C₆H₄) | PhsSPh | Ph-C(=CH–SPh)–CH₂–O–CH₂–(3-NC-C₆H₄) | 79 |
| Ph-C(=CH–I)–CH₂–O–C(O)NMe₂ | PhsSPh | Ph-C(=CH–SPh)–CH₂–O–C(O)NMe₂ | 64 |
| Ph-C(=CH–I)–CH₂–O–CH₂–(4-EtO₂C-C₆H₄) | PhCHO | Ph-C(=CH–CH(Oh)Ph)–CH₂–O–CH₂–(4-EtO₂C-C₆H₄) | 79 |

The products shown in Table I were obtained with a trans/cis or cis/trans ratio of greater than 98:2 in each case.

B. Preparation of Grignard Compounds on a Polymer Support and Reaction with Electrophils 150 mg of Wang resin functionalized with cis-iodallyl ether were admixed with 2 ml of THF and cooled to −40° C. 1.25 ml (0.9 mmol) of a 0.72 M solution of isopropylmagnesium bromide in THF were added dropwise and, after 4 hours, 0.2 ml (1.88 mmol) of benzaldehyde was added. After incubation for 1 hour, the mixture was filtered, the residue was washed with THF and MeOH and the product was cleaved from the polymer using 4 ml of 95% strength trifluoroacetic acid.

Filtration and evaporation gave the corresponding products.

The substances shown in Table II were prepared analogously. The yield of free product was generally 90% or more (see Table, Column 5).

TABLE II

Preparation of Grignard compounds and reaction with electrophils on a solid support.

| Vinyl halide | Electrophil | Product* | Yield (%) |
|---|---|---|---|
| Ph-C(=CH–I)–CH₂–O–(P) | PhCHO | 2,5-dihydrofuran with Ph at 3- and 2-positions | 95 |

TABLE II-continued

Preparation of Grignard compounds and reaction with electrophils on a solid support.

| Vinyl halide | Electrophil | Product* | Yield (%) |
|---|---|---|---|
| 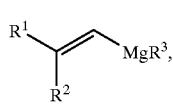 | PhCHO | 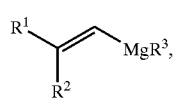 | 97 |

*Spontaneous cyclization to the dihydrofuran occurs after acid cleavage from the polymer The abbreviations for the electrophils in Tables I and II have the following meanings: PhCHO=benzaldehyde, TsCN=tosyl cyanide and PhsSPh=diphenyl disulfide.

We claim:

1. A process for preparing a compound of the formula I

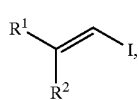
(I)

which comprises stereoselectively reacting compounds of the formula II (II)

with compounds of the formula $R^3MgX$ (III) at below +30° C. to give compounds of the formula I, where the substituents and variables in the formulae I, II and III have the following meanings:

X = halogen or $R^3$, $R^1$ = substituted or unsubstituted, branched or unbranched $C_1-C_{10}$-alkyl, $C_3-C_{10}$-cycloalkyl, $C_1-C_4$-alkylaryl, $C_1-C_4$-alkylheteroaryl, aryl or heteroaryl, $R^2$ = hydrogen or —$CH_2$—$R^4$, $R^3$ = branched or unbranched $C_1-C_{10}$-alkyl or $C_3-C_{10}$-cycloalkyl, $R^4$ = hydrogen, substituted or unsubstituted, branched or unbranched —$OC_1-C_{10}$-alkyl, —$OC_3-C_{10}$-cycloalkyl, —$OC_1-C_4$-alkylaryl, —$OC_1-C_4$-alkylheteroaryl, —$OCNR^1R^5$ or $R^6$, $R^5$ = as $R^1$, but independently thereof, $R^6$ = a solid support.

2. The process of claim 1 carried out in an inert aprotic solvent.

3. A process as claimed in claim 1 carried out at from −100° C. to +30° C.

4. The process of claim 1, wherein the reaction to form compounds of the formula I as claimed in claim 1 is complete within 18 hours.

5. The process of claim 1 wherein $R^2$ is —$CH_2$—$R^4$ and $R^4$ is a solid support (=$R^6$).

6. A compound of the formula Ia (Ia)

where the variables $R^1$ and $R^3$ have the meanings specified in claim 1, $R^2$ is —$CH_2$—$R^4$ and $R^4$ is $R^6$ and $R^6$ is a solid support.

7. The process of claim 1, wherein X is Cl.

* * * * *